United States Patent

Kalchauer et al.

Patent Number: 5,302,736
Date of Patent: Apr. 12, 1994

[54] PROCESS FOR THE REMOVAL OF HYDROGEN-CONTAINING SILANES FROM SILANES

[75] Inventors: Wilfried Kalchauer; Bernd Pachaly, both of Burghausen, Fed. Rep. of Germany

[73] Assignee: Wacker-Chemie GmbH, Munich

[21] Appl. No.: 143,593

[22] Filed: Nov. 1, 1993

[30] Foreign Application Priority Data

Dec. 10, 1992 [DE] Fed. Rep. of Germany ....... 4241696

[51] Int. Cl.$^5$ .............................. C07F 7/08; C07F 7/18
[52] U.S. Cl. ..................... 556/430; 556/466; 556/477
[58] Field of Search ................. 556/430, 466

[56] References Cited

U.S. PATENT DOCUMENTS 3,646,092 2/1972 Dathe ............................. 556/466
4,985,579 1/1991 Bokerman et al. ................. 556/466

Primary Examiner—Paul F. Shaver
Attorney, Agent, or Firm—Martin Connaughton

[57] ABSTRACT

The present invention is a process wherein silanes containing hydrogen atoms bonded directly to silicon are removed from silanes of the general formula $$R_xCl_{3-x}Si-[SiR_yCl_{2-y}]_n-A \qquad (I)$$

and mixtures thereof, in which R denotes an optionally halogen-substituted hydrocarbon radical having 1 to 18 carbon atoms which is free from ethylenic double bonds, A denotes a chlorine atom or a radical R, x has the value of 0, 1, 2 or 3, y has the value of 0, 1 or 2 and n has the value of 0 or 1. The silanes containing hydrogen atoms bonded directly to silicon are reacted with hydrogen chloride in the presence of silver or gold as catalysts to give the corresponding chlorosilanes.

4 Claims, No Drawings

PROCESS FOR THE REMOVAL OF HYDROGEN-CONTAINING SILANES FROM SILANES

FIELD OF INVENTION

The invention relates to a process for the removal of silanes containing hydrogen atoms bonded directly to silicon from hydrocarbon-silanes, hydrocarbon-halosilanes and halosilanes.

BACKGROUND OF INVENTION

In addition to the silanes of the general formula $Me_a\text{-}SiCl_{4-a}$, in which a has a value from 0 to 4 and Me here and below denotes a methyl group, small amounts of ethylchlorosilanes, various hydridosilanes, above all $Me_bHSiCl_{3-b}$, in which b has a value from 0 to 2, and ethyldichlorosilane $EtHSiCl_2$ are also formed during direct synthesis of methylchlorosilanes from silicon and methyl chloride at 250° to 300° C. using copper catalysts. The direct synthesis is described, inter alia, in W. Noll, Chemistry and Technology of Silicones, Academic Press, Inc., Orlando, Fla., 1968, chapter 2.2.

The most sought-after target product of the direct synthesis is $Me_2SiCl_2$, which can be converted by hydrolysis and polycondensation into silicone polymers having diverse functional groups and structures.

An essential feature of most silicone polymers is the lowest possible content of trifunctional impurities in the polymer skeleton. One of the possible trifunctional impurities of the $Me_2SiCl_2$ employed is $EtHSiCl_2$.

Since the boiling points of $Me_2SiCl_2$ (70°–71° C.) and $EtHSiCl_2$ (74°–76° C.) differ from one another by only about 4° C., a very distillative effort, such as high reflux ratios, a large number of theoretical plates, and trays in practice, a high energy requirement and a reduced space/time yield, are necessary in order to obtain the $Me_2SiCl_2$ in the purity required for the particular use.

EP-A 423,948 describes the removal of silanes containing hydrogen atoms bonded directly to silicon (H-silanes) from organosilane mixtures by reaction with hydrogen chloride gas in the presence of suitable catalysts from sub-group VIII of the Periodic Table, Pd, Pt, Rh, Ru, Ni, Os, Ir and compounds thereof, to give the corresponding alkylchlorosilanes. The difference in boiling points between the organosilanes desired and the impurity is increased by this measure such that the distillation can be operated with a considerably reduced effort.

The disadvantage of this known process is that the metals employed as catalysts, with the exception of nickel, are relatively expensive and that, if nickel is employed as the catalyst, relatively high catalyst concentrations are necessary and the conversions thereby achieved are low, and that the metals are in some cases too susceptible to catalyst poisons.

SUMMARY OF INVENTION

The invention relates to a process for the removal of silanes containing hydrogen atoms bonded directly to silicon from silanes of the general formula

$$R_xCl_{3-x}Si\text{—}[SiR_yCl_{2-y}]_n\text{—}A \quad (I)$$

and mixtures thereof, in which R denotes an optionally halogen-substituted hydrocarbon radical having 1 to 18 carbon atoms which is free from ethylenic double bond, A denotes a chlorine atom or a radical R, x has the value 0, 1, 2 or 3, y has the value 0, 1 or 2 and n has the value 0 or 1, in which the silanes containing hydrogen atoms bonded directly to silicon are reacted with hydrogen chloride in the presence of silver or gold as catalysts to give the corresponding chlorosilanes.

The H-silanes can be converted by the process according to the invention almost completely into higher-boiling chlorosilanes in which a chlorine atom is bonded at the position where the hydrogen atom was previously bonded. For example, tetrachlorosilane is formed from trichlorosilane, ethyltrichlorosilane is formed from ethyldichlorosilane and dimethyldichlorosilane is formed from dimethylchlorosilane. If they are not wanted in the product mixture, these chlorosilanes can easily be removed by distillation.

The reaction proceeds sufficiently quickly and with catalysts in the solid form. The reaction is thus catalyzed heterogeneously, so that the catalyst can be employed in a distillation column or in a flow-through reactor.

Silver is considerably cheaper than the metals Pd, Pt, Rh, Ru, Os and Ir used to date, and the reaction proceeds considerably faster with silver than with Ni.

Because of its very high normal potential in the electrochemical series of the elements, gold has a greater resistance to poisoning phenomena and undesirable reactions with alkylchlorosilanes or hydrogen chloride and therefore a longer life compared with the metals Pd, Pt, Rh, Ru, Os, Ni and Ir used to date.

Alloys of silver and gold can also be employed as catalysts in the process according to the invention.

The catalyst is preferably employed in finely divided form, in which case it is preferably on supports. Supports which carry both silver and gold can also be employed.

Examples of supports are active charcoal, charcoal and inorganic oxides, such as silicon dioxide, aluminum-(III) oxide, silicates, titanium dioxide and zirconium dioxide, carbides, such as silicon carbide; charcoal, active charcoal and silicon dioxide are preferred examples.

Such catalysts in which the finely divided metals are on supports can be prepared by reduction of metal compounds in the presence of the support.

The concentration of the metals on the supports is preferably 0.8 to 5% by weight, based on the total weight of the catalyst; however, it is also possible to use higher or lower concentrations.

Examples of hydrocarbon radicals R in the general formula I are alkyl radicals, such as the methyl, ethyl, n-propyl, iso-propyl, n-butyl, iso-butyl, tert-butyl, n-pentyl, iso-pentyl, neo-pentyl and tert-pentyl radical; hexyl radicals, such as the n-hexyl radical; heptyl radicals, such as the n-heptyl radical; octyl radicals, such as the n-octyl radical and iso-octyl radicals, such as the 2,2,4-trimethylpentyl radical; nonyl radicals, such as the n-nonyl radical; decyl radicals, such as the n-decyl radical; dodecyl radicals, such as the n-dodecyl radical; octadecyl radicals, such as the n-octadecyl radical; cycloalkyl radicals, such as cyclopentyl, cyclohexyl and cycloheptyl radicals and methylcyclohexyl radicals; aryl radicals, such as the phenyl, naphthyl, anthryl and phenanthryl radical; alkaryl radicals, such as o-, m- and p-tolyl radicals, xylyl radicals and ethylphenyl radicals; and aralkyl radicals, such as the benzyl radical and the α- and the γ-phenylethyl radical.

Examples of halogen-substituted radicals R are haloalkyl radicals, such as the 3,3,3-trifluoro-n-propyl radical, the 2,2,2,2',2',2'-hexafluoroisopropyl radical and the heptafluoroisopropyl radical, and haloaryl radicals, such as the o-, m- and p-chlorophenyl radical.

Preferred radicals R are unsubstituted hydrocarbon radicals, in particular those having 1 to 8 carbon atoms, specifically methyl, ethyl, tolyl and phenyl radicals. Preferably, n has the value 0.

Any desired H-silanes can be removed in the process according to the invention. The H-silanes have the general formula

$$R'_z SiH_{4-z} \qquad (II)$$

in which R' denotes an optionally halogen-substituted hydrocarbon radical having 1 to 18 carbon atoms and z has a value of from 0 to 3.

Examples of the radicals R' are the examples described above for R and alkenyl radicals, such as the vinyl and the allyl radical.

Preferred examples of H-silanes to be removed are silane, chlorosilane, dichlorosilane, trichlorosilane, methylsilane, methylchlorosilane, methyldichlorosilane, dimethylchlorosilane and ethyldichlorosilane.

The process according to the invention is particularly suitable for use in the purification of crude products and prepurified products from the direct synthesis of methylchlorosilanes, in particular dimethyldichlorosilane, which contain EtHSiCl$_2$ and possibly other by-products due to the direct synthesis. The by-products of the direct synthesis are described, for example, in W. Noll, Chemistry and Technology of Silicones, Academic Press, Inc., Orlando, Fla., 1968, chapter 2.2, and A. Hunyar, Chemie der Silikone (Chemistry of the Silicones), Verlag Technik, Berlin 1952, pages 92 to 94.

The concentration of H-silanes is usually 100 to 5000 ppm; however, the products from the methylchlorosilane synthesis which are to be purified can also contain higher or lower concentrations of H-silanes.

The process according to the invention is preferably carried out at a temperature of 50° to 150° C. under ambient pressure. However, higher or lower temperatures and pressures can also be used.

The catalyst used according to the invention can be employed in the liquid phase or in the gas phase.

For reasons of stoichiometry, at least one hydrogen chloride molecule must be employed per hydrogen atom for complete removal of the H-silanes. Hydrogen chloride gas is preferably employed in a stoichiometric excess, since by this means the residence times can be reduced and the degrees of conversion can be increased.

The process according to the invention can be carried out batchwise, semi-continuously or completely continuously, the completely continuous procedure preferably being employed.

In the continuous procedure, the residence time of the H-silanes in a preferred embodiment is 0.5 to 30 sec., depending on their initial concentration; however, longer or shorter residence times can also be chosen.

In the following examples, unless stated otherwise, (a) all amounts are based on weight; (b) all pressures are 0.10 MPa (absolute) and (c) all temperatures are 20° C.

Abbreviations used are, Me: methyl radical and Et: ethyl radical.

Preparation of the catalyst—35 g of active charcoal in piece form purified with nitric acid and dried—Conterbon BA from Lurgi, Frankfurt - were mixed with 5 g of silver nitrate, 140 ml of distilled water and 1 ml of acetic acid and the mixture was heated to 70° C. 3 ml of formaldehyde solution (37% strength) were then added, while stirring. The coated charcoal was separated from the liquid phase, washed with distilled water and dried at 120° C. under an oil pump vacuum for 10 hours. The silver content on the charcoal was about 1.8% by weight.

30 g of active charcoal in piece form purified with nitric acid and dried—Conterbon BA from Lurgi, Frankfurt—were mixed with 2.5 g of tetrachloroauric acid, 300 ml of distilled water and 8 ml of concentrated hydrochloric acid and the mixture was heated to 80° C. 8 ml of formaldehyde solution (37% strength) were then added, while stirring. The coated charcoal was separated from the liquid phase, washed with distilled water and dried at 120° C. under an oil pump vacuum for 10 hours. The gold content on the charcoal was about 0.23%.

EXAMPLES 1 AND 2

Examples 1 and 2 shown in Table I are according to the invention

EXAMPLE 3

Example 3 shown in Table I was not conducted according to the invention.

110 g of a mixture of Me$_2$SiCl$_2$ and 520 ppm of EtHSiCl$_2$ were initially introduced into a three-necked flask equipped with a dropping funnel, gas inlet tube and a mirrored-glass column fitted with a distillation head under an argon atmosphere. A measured amount of catalyst (see col. A, Table I) was introduced into the mirrored-glass column.

The silane in the flask was heated to 70° C., while stirring, and hydrogen chloride was passed into the mixture at a rate of 4 l/hour. The evaporated silanes and the hydrogen chloride gas were passed through the column, condensed in the distillation head and taken off. Me$_2$SiCl$_2$/EtHSiCl$_2$ (520 ppm) was metered into the flask at the rate at which the distillate was removed from the system.

Each sample was allowed to react for a specific period of time (see col. B, Table I). The reaction was then discontinued and the distillate was analyzed by GC.

The amount of distillate after the stated reaction time was recorded for each sample (see col. C, Table I). The mass flow (ml/hour) and residence time in seconds, based on gaseous Me$_2$SiCl$_2$ over the catalyst were recorded in Table I, columns D and E respectively. The concentration of EtHSiCl$_2$ in the distillate was in ppm and record in column F.

TABLE I

| Example | Catalyst | A (g) | B (min) | C (ml) | D (ml/h) | E (s) | F (ppm) |
|---|---|---|---|---|---|---|---|
| 1 | gold/active charcoal (0.23%)*) | 17 | 125 | 250 | 120 | 2.6 | 35 |
| 2 | silver/active charcoal (1.8%)*) | 22 | 155 | 350 | 135 | 3.5 | 25 |
| 3 | active charcoal*) | 17 | 193 | 610 | 190 | 1.7 | 120 |

*)see preparation of the catalyst

EXAMPLE 4

According to the invention, the experimental set-up and procedure were as described in Example 1, with the modification that the silane employed had the following composition in % by weight: 60% of tetramethyldichlorodisilane, 34% of methyldichlorosilane and 6% remainder (various methylchloro-mono- and -disilanes).

20 g of silver-on-active charcoal (1.8%) were employed as the catalyst; the flask temperature was increased to 150° C., the mass flow was reduced to 50 ml/hour and the residence time was increased to 12 seconds. The resulting distillate had the following composition: 30% of tetramethyldichlorodisilane, 57% of methyltrichloroethane and 4% of methyldichlorosilane (degree of conversion based on HCl: 94%).

Tetramethyldichlorodisilane became concentrated in the reaction flask; methyldichlorosilane remained only in traces.

What is claimed is:

1. A process for the removal of silanes containing hydrogen atoms bonded directly to silicon from silanes of the general formula $$R_xCl_{3-x}Si-[SiR_yCl_{2-y}]_n-A \qquad (I)$$

and mixtures thereof, in which R denotes an a hydrocarbon which may be submitted with halogen radical having 1 to 18 carbon atoms which is free from ethylenic double bonds, A denotes a chlorine atom or a radical R, x has the value of 0, 1, 2 or 3, y has the value of 0, 1 or 2 and n has the value of 0 or 1, in which the silanes containing hydrogen atoms bonded directly to silicon are reacted with hydrogen chloride in the presence of silver or gold as catalysts to give the corresponding chlorosilanes.

2. The process as claimed in claim 1, wherein the catalyst is employed in finely divided form on supports.

3. The process as claimed in claim 1, wherein the silanes containing hydrogen atoms bonded directly to silicon are removed from product mixtures obtained during methylchlorosilane synthesis.

4. The process as claimed in claim 3, wherein EtSiHCl$_2$ is removed.

* * * * *